United States Patent [19]

Schmitt et al.

[11] Patent Number: 5,389,300
[45] Date of Patent: Feb. 14, 1995

[54] AGENT FOR PROTECTING SAWN TIMBER

[75] Inventors: Hans-Georg Schmitt, Krefeld; Otto Exner, Ratingen; Hans-Ulrich Buschhaus, Krefeld, all of Germany

[73] Assignee: Bayer Aktiengesellschaft, Leverkusen, Germany

[21] Appl. No.: 64,538

[22] Filed: May 19, 1993

[30] Foreign Application Priority Data

May 27, 1992 [DE] Germany ............... 4217523

[51] Int. Cl.⁶ ............... A01N 25/02; A01N 37/20
[52] U.S. Cl. ............... 252/380; 422/1; 514/646; 514/667; 514/671; 514/672
[58] Field of Search ............... 514/667, 672, 671, 646; 422/1; 252/380

[56] References Cited

U.S. PATENT DOCUMENTS

| | | | |
|---|---|---|---|
| 3,481,686 | 12/1969 | Ivnäs et al. | 422/32 |
| 3,923,870 | 12/1975 | Singer | 560/158 |
| 4,686,236 | 8/1987 | Schade et al. | 514/526 |
| 4,719,227 | 1/1988 | Schade et al. | 514/452 |
| 4,844,891 | 7/1989 | Rosen et al. | 514/244 X |
| 4,855,318 | 8/1989 | Schade et al. | 514/467 |
| 5,200,421 | 4/1993 | Ludwig et al. | 514/383 |

FOREIGN PATENT DOCUMENTS 1272558 8/1990 Canada .

Primary Examiner—Robert L. Stoll
Assistant Examiner—Valerie Fee
Attorney, Agent, or Firm—Sprung Horn Kramer & Woods

[57] ABSTRACT

The present invention relates to an agent or concentrate for protecting sawn timber against wood-discolouring fungi, containing a fungicide on phenol basis and a fungicide on organo-iodine basis, optionally fungicides and insecticides, dissolved in an organochemical solvent or solvent mixture or in a mixture of water and organochemical solvent or solvent mixture and at least one emulsifier.

7 Claims, No Drawings

AGENT FOR PROTECTING SAWN TIMBER

The present invention relates to an agent or concentrate for protecting sawn timber against wood-discolouring fungi.

Freshly sawn timber in the damp state is frequently infested with wood-discolouring fungi (bluestaining fungi) and moulds, causing the value of the wood to be reduced. It is therefore necessary to carry out a protective treatment.

It has been disclosed that iodopropargyl derivatives such as, for example, 3-iodo-2-propinyl-n-butylcarbamate (IPBC), are suitable in principle for use in wood protection (cf. DE-OS (German Published Specification) 2,433,410). These compounds are active against bluestaining fungi, but unsatisfactory when used individually against the broad range of the naturally occurring wood-discolouring fungi and moulds, since their spectrum of action is incomplete.

It is furthermore known that mixtures of IPBC and didecyldimethylammonium chloride can be employed for protection against wood-destroying fungi, mainly fungi causing brown rot and white rot, and against wood-discolouring fungi and against white ants (cf. AU 8656-411). Moulds and mildew can also be controlled with these mixtures. However, since the didecyldimethylammonium chloride derivatives are relatively highly corrosive, the applicability of such formulations for use in untreated metallic treatment basins, in particular treatment basins made of iron, is limited. Moreover, formulations of this type tend to foam due to the surface activity of quaternary ammonium salts, so that an addition of defoamers may be required.

It is furthermore known that phenolic active compounds such as, for example, pentachlorophenol, or their alkali metal salts can be employed for protecting sawn timber against wood-discolouring fungi; the use in particular of pentachlorophenol or of its alkali metal salts, however, is disadvantageous due to toxicological and ecotoxicological properties of these compounds.

It is furthermore known that halogen-free phenol derivatives such as, for example, ortho-phenylphenol or their alkali metal salts can be used for protecting sawn timber against fungal infestation. Even though the use of these compounds is acceptable from the toxicological and ecotoxicological point of view, they are unsatisfactory when used individually against the broad spectrum of the naturally occurring wood-discolouring fungi and moulds since their spectrum of action is incomplete.

Surprisingly, it has now been found that new active compound combinations of at least one phenol derivative such as, for example,
tribromophenol
tetrachlorophenol
3-methyl-4-chlorophenol
dichlorophene
o-phenylphenol
m-phenylphenol
p-phenylphenol
2-benzyl-4-chlorophenol
or their metal salts, very particularly preferably o-phenylphenol, and at least one iodopropargyl derivative of the formula (I)

$$IC \equiv C-CH_2-O-CO-NH-R \qquad (I)$$

in which

R represents straight-chain or branched alkyl having 1 to 6 carbon atoms, cycloalkyl having 3 to 6 carbon atoms or aryl, preferably phenyl,
have a particularly broad and high activity against wood-discolouring and wood destroying fungi and moulds, combined with low concentrations on use.

In particular, it could not have been expected that the iodopropargyl derivatives form with the acidic phenol derivatives mixtures which are stable for a prolonged period without decomposition.

Examples of iodopropargyl derivatives which may preferably be mentioned are:
3-iodo-2-propinyl n-butylcarbamate (IPBC)
3-iodo-2-propinyl n-hexylcarbamate
3-iodo-2-propinyl cyclohexylcarbamate
3-iodo-2-propinyl phenylcarbamate
very particularly preferably
3-iodo-2-propinyl n-butylcarbamate (IPBC).

The combination of o-phenylphenol and IPBC must be emphasised very particularly.

The phenyl derivatives can exist not only in the form of free acids but also—as already mentioned—in the form of their metal salts. Suitable metals are preferably metals from group IA of the periodic table such as, for example, lithium, sodium or potassium.

The ratios by weight of the active compounds in the active compound combinations can be varied within relatively large ranges.

The mixtures contain from 0.1 to 99.9% of the phenol component, the remainder to 100% being the iodopropargyl compound.

The mixing ratio of phenol component to iodopropargyl compound is preferably 75:1 to 1:1, particularly preferably 50:1 to 5:1.

The active compound combinations according to the invention have a powerful action against micro-organisms; they are active mainly against moulds and wood-discolouring fungi as well as wood destroying fungi and can therefore be employed for the protection of sawn timber.

The new active compound combinations can be applied in the form of concentrates and the use forms prepared therefrom, such as solutions, suspensions, emulsions or pastes.

The application for the protection of the wood can be effected, for example depending on the extent to which the wood is endangered or on the prevailing technolgical facilities,
 a) by spraying the wood with solutions or emulsions,
 b) by immersing the wood into solutions or emulsions,
 c) by painting the wood with solutions or emulsions The amount of active compound combinations employed depends on the nature and the occurrence of the microorganisms, and the microbial count and on the medium. The optimal dosage rate can be determined in each case on use, using test series. However, in general it suffices to employ 0.01 to 2 g/m², preferably 0.05 to 1 g/m², of the active compound mixtures based on the surface area of the sawn timber to be protected.

The formulations mentioned can be prepared in a manner known per se, for example by dissolving the active compounds in a solvent or diluent and, if appropriate, further auxiliaries such as emulsifiers, or by emulsifying emulsifier-containing organic solutions in water.

Suitable solvents or diluents are organochemical solvents or solvent mixtures and/or a polar organic solvent or solvent mixture and/or an oily or oil-type organo-chemical solvent or solvent mixture and/or water with at least one emulsifier and/or wetting agent.

Unpolar organochemical solvents or solvent mixtures which are employed are oily or oil-type solvents with low volatility such as mineral oils or mineral oil-containing solvent mixtures, white spirit, petroleum and/or alkylbenzene.

Polar organochemical solvents which are employed are solvents or solvent mixtures which contain hydroxyl, ester, ether or keto groups, preferably dibutyl phthalate or butyl benzoate.

Other substances which can additionally be used are ester alcohols such as, for example, 2,2,4-trimethylpentanediol monoisobutyrate and/or other ester alcohols having a similar structure.

Emulsifiers or emulsifier mixtures which arrive are nonionic emulsifiers such as, for example, alkyl polyglycol ethers or alkylaryl polyglycol ethers or anionic emulsifiers such as, for example, alkylbenzenesulfonic acids or salts of the alkylbenzenesulfonic acids or alkylcarboxylic acids such as stearic acid or ricinoleic acid or their alkali metal salts or ammonium salts or mixtures of different non-ionic and or anionic emulsifiers. Mixtures of dodecylbenzenesulfonates with ricinoleates are preferably used.

Other fungicides, insecticides or other active compounds can be added to the active compound combinations according to the invention, the agents, concentrates or quite generally formulations which can be prepared therewith, to increase the spectrum of action or to achieve specific effects. Particularly favourable components for mixtures are, for example, the following compounds:

Sulfenamides such as dichlorofluanide, tolylfluanide, folpet, fluorofolpet;
Benzimidazoles such as carbendazime, benomyl, fuberidazole, thiabendazole or their salts,
Thiocyanates such as thiocyanatomethylthiobenzothiazole, methylene bisthiocyanate;
quaternary ammonium compounds such as benzyldimethyltetradecylammonium chloride, benzyldimethyldodecylammonium chloride, didecyldimethylammonium chloride;
Morpholino derivatives such as tridemorph, fenpropimorph, falimorph.
Azoles such as triadimefone, triadimenole, bitertanol, tebuconazole, propiconazole, azaconazole, hexaconazole, propchlorazo:
Iodine derivatives such as diiodomethyl p-tolyl sulfone, 3-iodo-2-propinylalcohol, 4-chlorophenyl-3-iodopropargyl-formal, 3-bromo-2,3-diiodo-2-propenylethylcarbonate 2,3,3-triiodoallylalcohol, 3-bromo-2,3-diiodo-2-propenylalcohol;
Bromine derivatives such as bronopol;
Isothiazolinones such as N-methylisothiazolin-3-one, 5-chloro-N-methyl-isothiazolin-3-one, 4,5-dichloro-N-octylisothiazolin-3-one, N-octyl-isothiazolin-3-one;
Benzisothiazolinones, cyclopenteneisothiazolinones;
Pyridines such as 1-hydroxy-2-pyridinethione (and their Na, Fe, Mn and Zn salts), tetrachloro-4-methylsulfonylpyridine;
Metallic soaps such as tin naphthenate, tin octoate, tin 2-ethylhexanoate, tin oleate, tin phosphate, tin benzoate, copper napthenate, copper octoate, copper 2-ethylhexanoate, copper oleate, copper phosphate, copper benzoate, zinc naphthenate, zinc octotate, zinc 2-ethylhexanoate, zinc oleate, zinc phosphate and zinc benzoate;
Oxides such as tributyltin oxide, $Cu_2O$, $CuO$, $ZnO$;
Dialkyldithiocarbamates such as Na and Zn salts of dialkyldithiocarbamates, tetramethylthiuram disulfide;
Nitriles such as 2,4,5,6-tetrachloroisophthalodinitrile;
Benzothiazoles such as 2-mercaptobenzothiazole;
Quinolines such as 8-hydroxyquinoline;
Boron compounds such as boric acid, boric esters, borax;
Formaldehyde-releasing compounds such as benzyl alcohol mono(poly)-hemiformal, oxazolidines, hexahydro-S-triazines, N-methylolchloroacetamide;
Tris-N-(cyclohexyldiazeniumdioxy)-aluminium, N-(cyclohexyldiazeniumdioxy)-tributyltin or K' salts, bis-N-(cyclohexyldiazeniumdioxy)-copper.

Carbonic acids such as benzoic acid, sorbinic acid, 2-Ethylhexanoic acid as well as their alkali- and earth-alkali-salts.

Insecticides which are preferably added are:
Phosphoric esters such as azinphos-ethyl, azinphos-methyl, 1-(4-chlorophenyl)-4-(O-ethyl, S-propyl)-phosphoryloxypyrazole, chloropyrifos, coumaphos, demeton, demeton-S-methyl, diazinone, dichlorvos, dimethoate, ethoprophos, etrimfos, fenitrothion, penthion, heptenophos, parathion, parathion-methyl, phosalone, phoxim, pirimiphos-ethyl, pirimiphos-methyl, profenofos, prothiofos, sulfprofos, triazophos and trichlorophone;
Carbamates such as aldicarb, bendiocarb, 2-(1-methylpropyl)phenyl methyl carbamate, butocarboxim, butoxycarboxim, carbaryl, carbofuran, carbosulfan, cloethocarb, isoprocarb, methomyl, oxamyl, pirimicarb, promecarb, propoxur and thiodicarb;
Pyrethroids such as allethrin, alphamethrin, bioresmethrin, byfenthrin, cycloprothrin, cyfluthrin, decamethrin, cyhalothrin, cypermethrin, deltamethrin, alpha-cyano-3-phenyl-2-methylbenzyl 2,2-dimethyl-3-(2-chloro-2-trifluoro-methylvinyl)-cyclopropanecarboxylate, fenpropathrin, fenfluthrin, fenvalerate, flucythrinate, flumethrin, fluvalinate, permethrin, resmethrin and tralomethrin;
Nitroimines and nitromethylenes such as 1-[(6-chloro-3-pyridinyl)-methyl]-4,5-dihydro-N-nitro-1H-imidazol-2-amine(imidacloprid), Novel agents or concentrates contain the active compound mixtures according to the invention in a concentration of from 0.01 to 80% by weight, besides, if appropriate, 0.001 to 10% by weight of a suitable other fungicide or insecticide, as mentioned above, as well as more than 20% by weight of a mixture of solvent/diluent, if appropriate emulsifiers and, if appropriate, water.

If an insecticide is present, the agents, concentrates and formulations according to the invention, for the protection of sawn timber, which have been prepared in this manner have an activity not only against the above-mentioned fungi but also against wood-destroying insects.

The concentrate according to the invention for the protection of sawn timber against wood-discolouring fungi, wood destroying fungi as well as moulds advantageously contains 20 to 60% by weight, preferably 30 to 60% by weight, particularly preferably 50 to 55% of the mixture of A) ortho-phenylphenol and B) iodopropargyl butylcarbamate in a ratio of 75:1 to 1:1, preferably 50:1 to 5:1, as well as 0 to 15% by weight, preferably 2 to 10% by weight, of ester alcohols, 5 to 25% by weight, preferably 10 to 15% by weight, of anionic emulsifiers or emulsifier mixtures and 0 to 75% by weight, preferably 20 to 38% by weight, of solvent, preferably phthalic acid or benzoic acid.

The agent according to the invention (ready-for-use agent) for the protection of sawn timber against wood-discolouring fungi contains, in an advantageous embodiment, 0.02 to 5.0% by weight, preferably 0.10 to 2.5% by weight, of a concentrate of 20 to 60% by weight, preferably 30 to 60% by weight, particularly preferably 50 to 55% by weight, of the mixture of A) ortho-phenylphenol B) iodopropargyl butylcarbamate in a ratio of 75:1 to 1:1, preferably 50:1 to 5:1, as well as 0 to 15% by weight, preferably 2 to 10% by weight, of ester alcohols, 5 to 25% by weight, preferably 10 to 15% by weight, of anionic emulsifiers or emulsifier mixtures and 0 to 75% by weight, preferably 20 to 38% by weight, of solvent, preferably phthalic esters or benzoic esters, diluted with more than 95.0% by weight, preferably more than 97.5% by weight, of water and/or solvent/diluent, preferably water.

The sawn timber is treated with the agent or concentrate according to the invention in such a way that 0.01 to 2 g/m$^2$, preferably 0.05 to 1 g/m$^2$, of the active compound combination are applied to the wood surface.

EXAMPLES

Example 1

300 g of o-phenylphenol are mixed with 10 g of iodopropargyl butylcarbamate in 410 g of butyl benzoate, treated with 30 g of 2,2,4-trimethylpentanediol monoisobutyrate and 250 g of an emulsifier mixture consisting of 25% by weight of sodium ricinoleate,
25% by weight of sodium dodecylbenzenesulfonate,
17% by weight of water and
33% by weight of butanol and the mixture is stirred for 4 hours at room temperature. 1000 g of a clear pale brown solution result, solidification point < −10° C.

Example 2

300 g of o-phenylphenol are mixed with 30 g of iodopropargyl butylcarbamate in 390 g of butyl benzoate, treated with 30 g of 2,2,4-trimethylpentanediol monoisobutyrate and 250 g of an emulsifier mixture consisting of 25% by weight of sodium ricinoleate,
25% by weight of sodium dodecylbenzenesulfonate,
17% by weight of water and
33% by weight of butanol and the mixture is stirred for 4 hours at room temperature. 1000 g of a clear, pale brown solution result, solidification point < −10° C.

Example 3

500 g of o-phenylphenol are mixed with 50 g of iodopropargyl butylcarbamate in 170 g of butyl benzoate, treated with 30 g of 2,2,4-trimethylpentanediol monoisobutyrate and 250 g of an emulsifier mixture consisting of 25% by weight of sodium ricinoleate,
25% by weight of sodium dodecylbenzenesulfonate,
17% by weight of water and
33% by weight of butanol and the mixture is stirred for 4 hours at room temperature. 1000 g of a clear pale brown solution result,
solidification point < 10° C.

Example 4

300 g of o-phenylphenol are mixed with 30 g of iodopropargyl butylcarbamate in 390 g of butyl benzoate, treated with 30 g of 2,2,4-trimethylpentanediol monoisobutyrate and 250 g of an emulsifier mixture consisting of 25% by weight of sodium ricinoleate,
25% by weight of sodium dodecylbenzenesulfonate,
17% by weight of water and
33% by weight of butanol and the mixture is stirred for 4 hours at room temperature. 1000 g of a clear pale brown solution result,
solidification point < 5° C.

Example 5

1 g of the concentrate of Example 1 are mixed with 999 g of tap water (∼20° German hardness) for 5 minutes;

a milky emulsion which remains stable for weeks without decomposition forms.

Example 6

15 g of the concentrate of Example 4 are mixed with 985 g of tap water (∼20° German hardness) for 5 minutes;

a milky emulsion which remains stable over weeks results.

This emulsion is not corrosive to steel compared with water.

Example 7 (Comparison Example)

300 g of o-phenylphenol are mixed with 420 g of butyl benzoate, treated with 30 g of 2,2,4-trimethylpentanediol monoisobutyrate and 250 g of an emulsifier mixture consisting of 25% by weight of sodium ricnoleate
25% by weight of sodium dodecylbenzenesulfonate,
17% by weight of water and
33% by weight of butanol and the mixture is stirred for 4 hours at room temperature. 1000 g of a clear pale brown solution result
solidification point < 5° C.

Example 8

Chips of pine sap-wood having a size of approximately 4 cm × 4 cm × 0.1 cm are autoclaved and impregnated in vacuo (10 minutes, 40 mbar) with sterile 1% strength malt extract solution.

The chips are then immersed for 1 minute in fungicide emulsion prepared with the concentrates of Examples 1, 2 and 7 by the procedure mentioned in Example 5 and 6; the following dilutions in tap water were selected:

With concentrate of Example 1: 0.1; 0.2; 0.5; 1.0; 1.5% by weight
With concentrate of Example 2: 0.1; 0.2; 0.5; 1.0; 1.5% by weight
With concentrate of Example 7: 1.0; 1.5; 2.0; 2.5; 3.0% by weight The impregnated wood chips treated with fungicide emulsion are stored for 24 hours and then contaminated with in each case 2 ml spore suspension of one of the following mixed inocula and incubated in sealed Petri dishes for 14 days at room temperature:

| Mixed inoculum A: | Aureobasidium pullulans |
|---|---|
| | Sclerophoma pityophila |
| Mixed inoculum B: | Trichoderma pseudokoningii |
| | Gliocladium virens |
| | Aspergillus niger |
| | Ceratocystis pilifera |
| | Phialophora fastigiata |
| | Penicillium sp. |

After the 14 days have elapsed, the chips are compared; the following numerical values indicate the concentrate contents in the emulsions in % by weight at which fungal growth is no longer observed:

| | Mixed inoculum | |
|---|---|---|
| | A | B |
| Concentrate of Example 1 | >0.1 - >0.2 | >0.2 - >0.5 |
| Concentrate of Example 2 | ~0.1 | ~0.2 |
| Concentrate of Example 7 | ~3.0 | >2.0 - <2.5 |

We claim:
1. A microbicidal composition consisting of ingredients (a) and (b) and optionally ingredients (c), (d) and/or (e), wherein ingredients (a), (b), (c), (d) and (e) are as follows:
(a) at least one phenol compound selected from the group consisting of tribromophenol, 3-methyl-4-chlorophenol, dichlorophene, o-phenylphenol m-phenylphenol, p-phenylphenol and 2-benzyl-4-chlorophenol, or a Group 1 A metal salt thereof;
(b) at least one iodopropargyl compound of the formula (I):

$$IC\equiv C-CH_2-O-CO-NH-R \qquad (I)$$

in which
R represents straight-chain or branched alkyl having 1 to 6 carbon atoms, cycloalkyl having 3 to 6 carbon atoms or aryl;
(c) a solvent or a diluent or a mixture thereof;
(d) an emulsifier or emulsifier mixture; and
(e) one or more microbially active compounds selected from the group consisting of dichlorofluanide, tolylfluanide, folpet, fluorofolpet, or carbendazime, benomyl, fuberidazole, thiabendazole or a salt thereof, thiocyanatomethyl benzothiazole, methylene bisthiocyanate, benzyl-dimethyltetradecylammonium chloride, benzyl-dimethyldodecylammonium chloride, didecyl-dimethylammonium chloride, tridemorph, fenpropimorph, falimorph, diiodomethyl p-tolyl sulfone, 3-iodo-2-propinyl alcohol, 4-chlorophenyl-3-iodopropargyl-formyl, 3-bromo-2,3-diiodo-2-propenylethylcarbonate, 2,3,3-triiodoallylalcohol, 3-bromo-2,3-diiodo-2-propenyl alcohol, bronopol, N-methyl isothiazolin-3-one, 5-chloro-N-methyl-isothiazolin-3-one, 4,5-dichloro-N-octyl isothiazolin-3-one, N-octyl-isothiazolin-3-one, benzoisothiazolinones, cyclopenteneisothiazolinones, 1-hydroxy-2-pyridinethione or a Na, Fe, Mn or Zn salt thereof, tetrachloro-4-methylsulfonylpyridine, tin octoate, tin 2-ethylhexanoate, tin oleate, tin phosphate, tin benzoate, copper octoate, copper 2-ethylhexanoate, copper oleate, copper phosphate, copper benzoate, zinc octotate, zinc 2-ethylhexanoate, zinc oleate, zinc phosphate, zinc benzoate, tributyltin oxide, $Cu_2O$, CuO, ZnO, a Na or Zn salt of a dialkyldithiocarbamate, tetramethylthiuram disulfide, 2,4,5,6-tetrachloroisophthalodinitrile, 2-mercaptobenzothiazole, 8-hydroxyquinoline, boric acid, a boric acid ester, borax, benzyl alcohol mono(poly)-hemiformal a oxazolidine, a hexahydro-S-triazine, N-methylolchloroacetamide, tris-N-(cyclohexyldiazenium dioxy)-aluminum, N-(cyclohexyldiazeniumdioxy)-tributyltin or a K salt thereof, bis-N-(cyclohexyldiazeniumdioxy)-copper, or benzoic acid, sorbinic acid or 2-ethyl hexanoic acid or an alkali- or earth-alkali-salt thereof, azinophos-ethyl, azinphos-methyl, 1-(4-chlorophenyl)-4-(O-ethyl, S-propyl)-phosphoryloxypyrazole, chloropyroifos, coumaphos, demeton, demeton-S-methyl, diazinone, dichlorvos, dimethoate, ethoprophos, etrimfos, fenitrothion, penthion, heptenophos, parathion, parathion-methyl, phosalone, phoxim, pirimiphos-ethyl, pirimiphos-methyl, profenofos, prothiofos, sulfprofos, triazophos, trichlorophone, aldicarb, bendiocarb, 2-(1-methylpropyl)phenyl methyl carbamate, butocarboxim, butoxycarboxim, carbaryl, carbofuran, carbosulfan, cloethocarb, isoprocarb, methomyl, oxamyl, pirimicarb, promecarb, propoxur, thiodicarb, allethrin, alphamethrin, bioresmethrin, byfenthrin, cydoprothrin, cyfluthrin, decamethrin, cyhalothrin, cypermethrin, deltamethrin, alpha-cyano-3-phenyl-2-methylbenzyl 2,2-dimethyl-3-(2-chloro-2-trifluoro-methylvinyl)cyclopropanecarboxylate, fenpropathrin, fenfluthrin, fenvalerate, flucythrinate, flumethrin, fluvalinate, permethrin, resmethrin, tralomethrin, and 1-[(6-chloro-3-pyridinyl)-methyl]-4,5-dihydro-N-nitro-1H-imidazil-2-amine.
2. Composition according to claim 1, characterised in that it contains an active compound combination consisting of ortho-phenylphenol and 3-iodo-2-propinyl n-butylcarbamate (IPBC).
3. Composition, according to claim 2, characterised in that it contains 20 to 60% by weight of the combination of
ortho-phenylphenol and
3-iodo-2-propinyl n-butylcarbamate (IBPC) in a ratio of 75:1 to 1, and further comprising
0 to 15% by weight of ester alcohols
5 to 25% by weight of anionic emulsifiers or emulsifier mixtures and
0 to 75% by weight of solvents.
4. Composition according to claim 3 wherein said solvents are solvents which contain polar organochemical hydroxyl, ether, ester or keto groups.
5. Method of protecting sawn timber against wood-discolouring fungi, wood-destroying fungi and molds, characterized in that 0.01 to 2 g/m² of the microbial composition according to claim 1, are applied to the timber surface.
6. Composition, characterized in that it contains (1) 0.02 to 5.0% by weight of a concentrate of:
20 to 60% by weight of ortho-phenylphenol and iodopropargyl butylcarbamate, in a ratio of from 75:1 to 1:1,
0-15% by weight of ester alcohols,
5-25% by weight of anionic emulsifiers or emulsifier mixtures,
0-75% by weight of solvents,
and (2) 95 to 99.8% by weight water.
7. Composition according to claim 6, characterised in that alkylbenzenesulfonates and/or alkylcarboxymates, and alkali metal or ammonium salts of ricinoleic acid, are employed as anionic emulsifiers.

* * * * *

UNITED STATES PATENT AND TRADEMARK OFFICE
CERTIFICATE OF CORRECTION

PATENT NO. : 5,389,300
DATED : February 14, 1995
INVENTOR(S) : Schmitt, et al.

It is certified that error appears in the above-indentified patent and that said Letters Patent is hereby corrected as shown below:

Col. 7, line 59-60   Delete " cydopenteneisothiazolinones " and substitute -- cyclopenteneisothiazolinones --

Col. 8, line 10   Delete " add " and substitute -- acid --

Col. 8, line 24   Delete " cydoprothrin " and substitute -- cycloprothrin --

Col. 8, line 33   Delete " imidazil " and substitute -- imidazol --

Col. 8, line 42   After " to " insert -- 1: --

Col. 8, line 55   After " Composition " insert -- according to claim 1 --

Signed and Sealed this

Eighteenth Day of April, 1995

Attest:

BRUCE LEHMAN

*Commissioner of Patents and Trademarks*

*Attesting Officer*